United States Patent
Gajji et al.

(10) Patent No.: US 10,281,381 B2
(45) Date of Patent: May 7, 2019

(54) AXIAL FLOW VISCOMETER

(71) Applicant: Halliburton Energy Services, Inc., Houston, TX (US)

(72) Inventors: Bhargav Gajji, Cypress, TX (US); Richard Gary Morgan, Channelview, TX (US); Ketan Chimanlal Bhaidasna, Houston, TX (US); Subrahmanyam Surya Venkata Sista, Hyderabad (IN)

(73) Assignee: Halliburton Energy Services, Inc., Houston, TX (US)

( * ) Notice: Subject to any disclaimer, the term of this patent is extended or adjusted under 35 U.S.C. 154(b) by 113 days.

(21) Appl. No.: 15/543,085

(22) PCT Filed: Mar. 18, 2015

(86) PCT No.: PCT/US2015/021282
§ 371 (c)(1),
(2) Date: Jul. 12, 2017

(87) PCT Pub. No.: WO2016/148711
PCT Pub. Date: Sep. 22, 2016

(65) Prior Publication Data
US 2018/0017476 A1  Jan. 18, 2018

(51) Int. Cl.
*G01N 11/10* (2006.01)
*G01N 11/16* (2006.01)
*G01N 33/28* (2006.01)

(52) U.S. Cl.
CPC ............ *G01N 11/10* (2013.01); *G01N 11/16* (2013.01); *G01N 33/28* (2013.01)

(58) Field of Classification Search
CPC ...... G01N 11/162; G01N 11/00; G01N 11/10; G01N 11/105; G01N 11/15; G01N 11/142; G01N 11/16; G01N 11/165
See application file for complete search history.

(56) References Cited

U.S. PATENT DOCUMENTS 2,607,217 A   8/1952  Merten et al.
3,073,150 A   1/1963  Fann
(Continued)

OTHER PUBLICATIONS

International Search Report and Written Opinion issued in related PCT Application No. PCT/US2015/021282 dated Nov. 23, 2015, 15 pages.

(Continued)

*Primary Examiner* — Justin N Olamit
(74) *Attorney, Agent, or Firm* — Tenley Krueger; Baker Botts L.L.P.

(57) ABSTRACT

Systems and methods for measuring the viscosity of a fluid comprises an oscillation cylinder having an inner surface, wherein the oscillation cylinder includes a fluid; a fixed piston having a first stopper disposed within the oscillation cylinder and forming a seal with the inner surface; an adjustable piston having a second stopper disposed within the oscillation cylinder and forming a seal with the inner surface; a chamber defined between the first stopper and second stopper; a bob formed within the chamber having a sensor which measures an axial shear force induced by the oscillating cylinder which is indicative of the apparent viscosity of the fluid in the chamber; and a motor capable of linearly translating the oscillation cylinder.

20 Claims, 1 Drawing Sheet

(56) References Cited

U.S. PATENT DOCUMENTS

| | | |
|---|---|---|
| 3,107,520 A | 10/1963 | Mouly et al. |
| 3,714,814 A | 2/1973 | Schneiders et al. |
| 4,005,599 A | 2/1977 | Schlatter et al. |
| 5,067,344 A | 11/1991 | Fitzgerald et al. |
| 6,571,609 B1 | 6/2003 | Bi |
| 6,951,127 B1 | 10/2005 | Bi |
| 7,412,877 B1 | 8/2008 | Bi |
| 9,291,585 B2 * | 3/2016 | Singh .................... G01N 25/00 |
| 2013/0243028 A1 | 9/2013 | Singh et al. |

OTHER PUBLICATIONS

International Preliminary Report on Patentability issued in related PCT Application No. PCT/US2015/021282 dated Sep. 19, 2017, 11 pages.

* cited by examiner

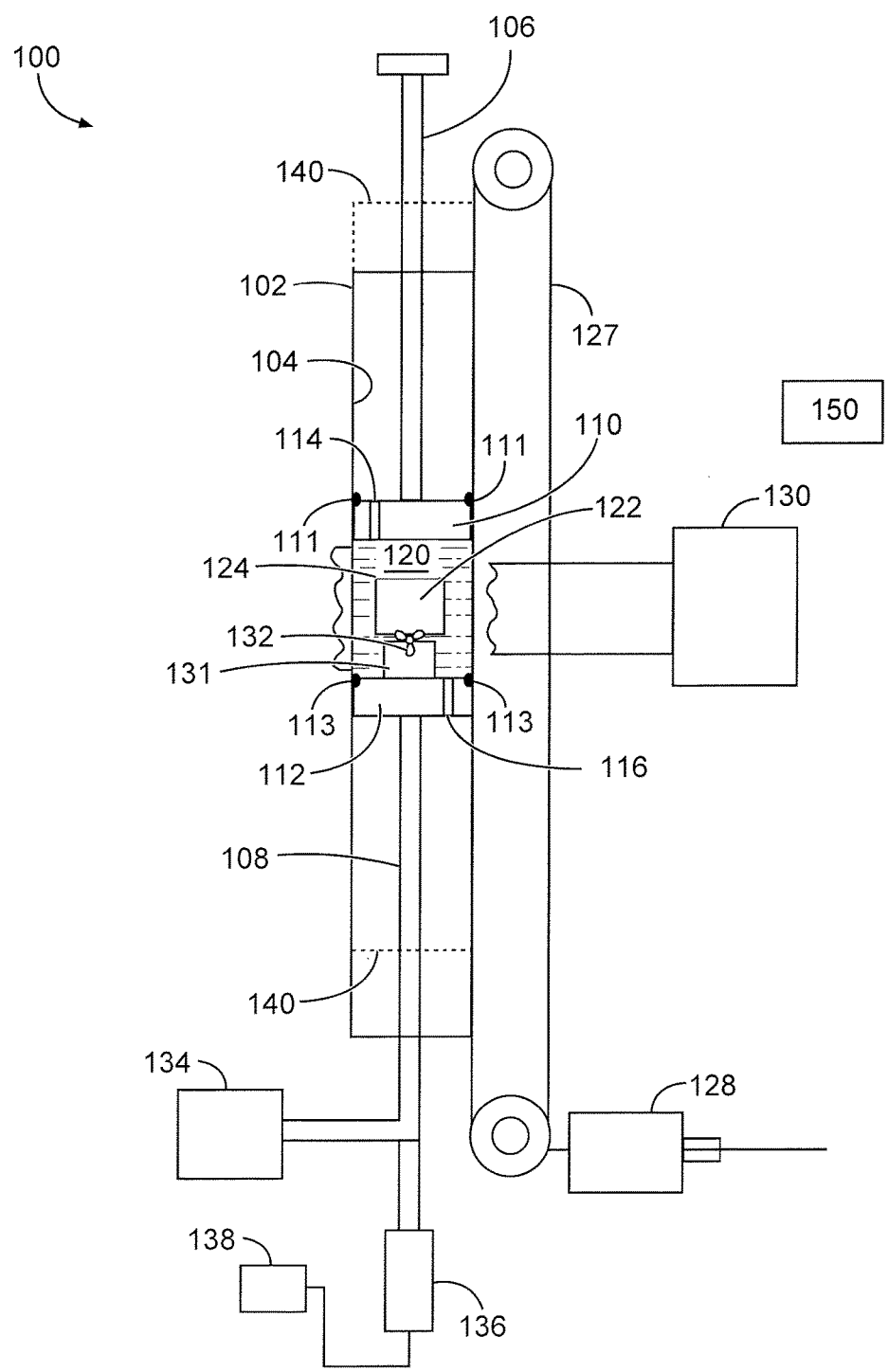

AXIAL FLOW VISCOMETER

CROSS-REFERENCE TO RELATED APPLICATION

The present application is a U.S. National Stage Application of International Application No. PCT/US2015/021282 filed Mar. 18, 2015, which is incorporated herein by reference in its entirety for all purposes.

BACKGROUND

The present disclosure relates generally to well drilling operations and, more particularly, to evaluate the properties of the fluids used in well drilling operations.

Hydrocarbons, such as oil and gas, are commonly obtained from subterranean formations that may be located onshore or offshore. The development of subterranean operations and the processes involved in removing hydrocarbons from a subterranean formation are complex. Typically, subterranean operations involve a number of different steps such as, for example, drilling a wellbore at a desired well site, cementing the well, treating the wellbore to optimize production of hydrocarbons, and performing the necessary steps to produce and process the hydrocarbons from the subterranean formation.

Various types of fluids are used in the oil and gas industry. Non-limiting examples include drilling muds, cement slurries, and stimulation treating fluids. Such fluids are typically pumped into oil or gas wells in known manners. It is desirable to know various characteristics of the fluids to determine how such fluids will act upon being pumped and placed in, or circulated through, the wells. For example, fluids used downhole are often exposed to unique conditions, including high pressures and temperatures.

Viscosity, elasticity, and consistency are rheological characteristics that sometimes need to be measured for a given fluid. Known devices used to test fluids for these characteristics include viscometers, rheometers, and consistometers. However, downhole pressures and temperatures may change the characteristics of a fluid. As a result, the fluid characteristics measured at the surface may be inconsistent with how the fluid behaves within the well environment. Fluids are typically chosen for an operation based on favorable properties, such as an ability to suspend particulates. It is therefore desirable to measure fluid properties, including viscosity, of a downhole fluid under downhole conditions before the fluid is placed in the well.

FIGURES

Some specific exemplary embodiments of the disclosure may be understood by referring, in part, to the following description and the accompanying drawings.

FIG. 1 is a diagram showing an illustrative viscosity measurement system, according to aspects of the present disclosure.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such as wires, optical fibers, microwaves, radio waves, and other electromagnetic and/or optical carriers; and/or any combination of the foregoing.

Illustrative embodiments of the present disclosure are described in detail herein. In the interest of clarity, not all features of an actual implementation may be described in this specification. It will of course be appreciated that in the development of any such actual embodiment, numerous implementation-specific decisions are made to achieve the specific implementation goals, which will vary from one implementation to another. Moreover, it will be appreciated that such a development effort might be complex and time-consuming, but would, nevertheless, be a routine undertaking for those of ordinary skill in the art having the benefit of the present disclosure.

The terms "couple" or "couples" as used herein are intended to mean either an indirect or a direct connection. Thus, if a first device couples to a second device, that connection may be through a direct connection or through an indirect mechanical or electrical connection via other devices and connections. Similarly, the term "communicatively coupled" as used herein is intended to mean either a direct or an indirect communication connection. Such connection may be a wired or wireless connection such as, for example, Ethernet or LAN. Such wired and wireless connections are well known to those of ordinary skill in the art and will therefore not be discussed in detail herein. Thus, if a first device communicatively couples to a second device, that connection may be through a direct connection, or through an indirect communication connection via other devices and connections.

Referring now to FIG. 1, an illustrative diagram of a viscosity measurement system 100 is shown, comprising an oscillation cylinder 102 having an inner surface 104, a first piston 106 and a second piston 108. The first piston 106 may be connected to a first stopper 110 disposed within the oscillation cylinder 102. The second piston 108 may be connected to a second stopper 112 disposed within the oscillation cylinder 102. The first stopper 110 may form a first seal 111 with the inner surface 104 and the second stopper 112 may form a second seal 113 with the inner surface 104.

A chamber 120 may be disposed within the oscillation cylinder 102, defined between the first stopper 110 and the second stopper 112, and the inner surface 104. A bob 122 may be formed and/or disposed within the chamber 120. In certain embodiments, the bob 122 may be connected to the second stopper 112.

In certain embodiments, a fluid may be placed within the chamber 120. In certain embodiments, the fluid may comprise any fluid or combination of fluids for use in a downhole environment. For example, the fluid may comprise a mud, oil well cements, and completion gels, and other fluids for use in the down-hole environment. In certain embodiments, the fluid may be a non-homogeneous fluid, a non-Newtonian fluid, a homogeneous fluid, a Newtonian fluid, or a combination of two or more such fluids.

The fluid within the chamber 120 may be in contact with the bob 122 and the inner surface 104. The bob 122 may comprise a sensor 124. The sensor may detect and/or measure a force exerted on the bob 122. For example, the sensor 124 may measure an axial shear force induced by the oscillation cylinder 102. The force detected and/or measured by the sensor 124 may be indicative of a force applied to the bob 122 by the fluid. For example, movement of the fluid within the chamber 120 may apply a force to the bob 122 (e.g., an axial shear force).

In certain embodiments, the oscillation cylinder 102 may be rotated using a motor as described below. As such, the bob 122 may comprise a rotation sensor, for example a torque transducer, that measures a force indicative of a rotational force applied to the bob 122 by the fluid.

In certain embodiments, the first stopper 110 may comprise a first valve 114 and/or the second stopper 112 may comprise a second valve 116. The first and second valve 114, 116 may be structured and arranged to selectively allow fluid flow into or out of the chamber 120. For example, the fluid may be placed into the chamber 120 through the first valve 114 or the second valve 116. After the fluid contained within the chamber 120, the valve 114, 116 may be closed to separate the chamber 120 from surrounding environment and prevent fluid flow out of the chamber 120. To remove fluid from the chamber 120, the first valve 114 and/or the second valve 116 may be opened and fluid may be directed out of the chamber 120.

The oscillation cylinder 102 may translate axially causing the inner surface 104 to apply a shear force to the fluid within the chamber 120. In response to the shear force, the fluid may be flow or otherwise move within the chamber 120 and exert a force on the bob 122. The force exerted on the bob 122 by the fluid in response to axial translation of the oscillation cylinder 102 may be indicative of one or more viscous properties of the fluid, including the apparent viscosity.

In certain embodiments, the bob 122 may comprise a load transducer; for example, the sensor 124 may include a load transducer. In certain embodiments, the system 100 may comprise a vortex generator 132 within the chamber and connected to the first or second stopper 110, 112 (shown in FIG. 1 connected to the second stopper 112). The vortex generator 132 may be capable of moving and/or circulating fluid within the chamber 120. In certain embodiments, the vortex generator 132 may circulate the fluid to facilitate fluid mixing, prevent settling of particulate matter, and/or reduce formation of eddy currents in the fluid. The vortex generator 132 may comprise a fan, rotor, turbine, or any other device capable of rotating fluid within the chamber 120.

In certain embodiments, a heating element 130 may be disposed adjacent to the oscillation cylinder 102. The heating element 130 may be capable of raising the temperature of the oscillation cylinder 102 and/or fluid within the chamber 103. In certain embodiments, the heating element 130 may raise the temperature of fluid within the chamber 103 to down-hole temperatures (i.e., the heating element 130 may be capable of simulating down-hole environment temperatures within the chamber 103). For example, the heating element 130 may be capable of bringing the temperature of the oscillation cylinder 102 and/or fluid within the chamber 103 to in the range of 25° C. to 250° C.

The system 100 may comprise an oscillation motor 128 capable of axially translating the oscillation cylinder 102. The oscillation motor 128 may be capable of oscillating the oscillation cylinder 102 relative to the chamber 120 and the bob 122 disposed within the chamber 120. In certain embodiments, the oscillation motor 128 may be capable of oscillating the oscillation cylinder 102 at a set frequency. For example, the motor 128 may translate the oscillation cylinder 102 from a first position (shown for example as the oscillation cylinder 120 current position) to a second position (represented by dashed-line 140), and then back to the first position. In certain embodiments, movement from the first position to second position back to first position may be considered as an oscillation. The oscillation motor 128 may translate the oscillation cylinder 102 at a velocity and/or frequency similar to that applied to the fluid in wellbore conditions. For example, the oscillation motor 128 may oscillate the oscillation cylinder 102 at a frequency of 1 oscillation per hour to 1000 oscillations per minute. For example, the oscillation motor 128 may be capable of translating the oscillation cylinder 102 at a velocity of 1 meter per hour to 100 kilometers per hour. For example, the oscillation motor 128 may be capable of accelerating the oscillation cylinder 102 at 0.1 km/s2 to 20 km/s2.

In certain embodiments, the oscillation motor 128 may comprise a stepper motor. The stepper motor may be capable of translating the oscillation cylinder 102 a set distance and then translating the oscillation cylinder 102 an equal set distance in the opposite direction (i.e. translating the oscillation cylinder to the second position then to the first position). The stepper motor may be capable of moving the oscillation cylinder 102 between the first and second positions at a set frequency.

In certain embodiments, a timing belt 127 may be connected to the oscillation motor 128 and engage the oscillation cylinder 102. The oscillation motor 128 may be structured and arranged to drive the timing belt 127 in a both clockwise and counterclockwise directions, causing the oscillation cylinder 102 to translate in opposite directions. In certain embodiments, the connection between the oscillation motor 128 and the timing belt 127 may comprise a linear actuator, for example complementary rack and pinion gears.

In certain embodiments, the first piston 106 may include a fixed piston. The fixed piston—and the first stopper 110 connected to the fixed piston—may be held in place within the oscillation cylinder 102. In certain embodiments, the second piston 108 may be an adjustable piston. The adjustable piston may translate axially within the oscillation cylinder 102, and translate the second stopper 112 within the oscillation cylinder 102. As such, the adjustable piston may decrease the volume of the chamber 120 by translating the second stopper 112 into the oscillation cylinder 102 toward the first stopper 110, or increase the volume of the chamber 120 by translating the second stopper 112 away from the oscillation cylinder 102.

In certain embodiments, a piston motor 138 may be connected to the second piston 108, and structured and arranged to translate the second piston 108 within the oscillation cylinder 102 toward or away from the first piston 106. In certain embodiments, the piston motor 138 may be connected to an extension member 136, where the extension member 136 engages the second piston 108. The piston motor 138 may translate the second piston 108 via the extension member 136. For example, in certain embodiments, the extension member 136 may comprise a screw or spindle. Rotation of the extension member 136 in an extension direction may extend the extension member 136, and the second piston 108, into the oscillation cylinder 102, and rotation of the extension member 136 in a retraction direction may move the extension member 136 and the second piston 108 in the opposite direction, away from the first piston 106.

In certain embodiments, the pressure within the chamber 120 may be increased or decreased by translating the adjustable piston toward or away from the fixed piston, respectfully. In certain embodiments, the oscillation cylinder 102 may be capable of containing a pressure of between 0.5 atmosphere and 250 atm. For example, in certain embodiments, the inner chamber 101 may be pressurized to at least 2 atm. In certain embodiments, the inner chamber 101 may be capable of containing a pressure of up to 500 atm.

In certain embodiments, the system 100 may comprise a rotation motor 134 connected to the second stopper 112 via the second piston 108. The rotation motor 134 may apply a torque to the second stopper 112 capable of rotating the second stopper 112 within the oscillation cylinder 102. In certain embodiments, the rotation motor 134 may be connected to the bob 122 and be capable of rotating the bob 122 within the chamber 120. In certain embodiments, the rotation motor 134 may be connected to the vortex generator 132 and capable of rotating the vortex generator 132 within the chamber 120.

In certain embodiments, the system 100 may comprise a magnet 131 connected to the second stopper 112. The bob 122 may be connected to the second stopper 112 via the magnet 131. For example, the magnet 131 may comprise an electromagnet, which may be energized to connect the bob 122 to the second stopper 112 and de-energized to release the bob 122. In certain embodiments, the position of the magnet 131 may be sensed using a magnetic sensor (not shown) disposed adjacent to the oscillation cylinder 102.

The sensor 124 may be capable of sending measurement data containing detected force applied to the bob 122 to a processor 150. In certain embodiments, the sensor 124, may comprise a processor. In other embodiments, the processor 150 may be part of a computer separate from the sensor 124. For example, the processor 150 may be in wireless communication with and capable of receiving measurement data in real-time from the sensor 114. Also for example, the measurement data may be sent to the processor 150 on a delayed basis, e.g., the measurement data may be sent to the processor 150 after the measurement data has been completely collected by the sensor 124. In certain embodiments, the magnetic sensor may transmit position data of the bob to the processor 150.

In certain embodiments, at least one of the motors 128, 138, and 134 may transmit viscometer status information (e.g., oscillation frequency and/or translation velocity measurements) to the processor 150. In certain embodiments, the magnetic sensor may transmit bob position information to the processor 150. The processor 150 may be configured to generate at least one human readable output using the measurement data and the movement data. For example, the processor 150 may correlate the measured shear force data in response to the movement data. For example, the processor 150 may output measurement data (e.g., instantaneous axial shear imparted to the bob and/or graph of axial shear over time), and/or manipulate the measurement data to output calculated viscosity.

In certain embodiments, one or more fluids having known fluid properties, such as viscosity, may be used to calibrate the system 100. After calibration, fluids having unknown viscosity properties may be measured by the system 100. For example, measurements observed by the sensor 124 for fluids having unknown properties may be compared to measurements from known fluids to determine to which known fluid the unknown fluid is most similar, in terms of viscosity profile.

In certain embodiments, the oscillation motor may oscillate the oscillation cylinder around the chamber containing the fluid set frequency. Axial translation of the oscillation cylinder may apply an axial shear force to the fluid within the chamber. In certain embodiments, the oscillation motor may adjust the oscillation frequency, the translation velocity, and/or the translation acceleration of the oscillation cylinder (increasing or decreasing each). In certain embodiments, the oscillation frequency, the maximum translation velocity, and/or the acceleration rate of the oscillation cylinder may be adjusted independently by making adjustments to the distance the oscillation cylinder translates. For example, in certain embodiments, oscillation frequency may be increased while keeping maximum translation velocity constant by decreasing an oscillation distance between the first position and the second position of the oscillation cylinder. Similarly, the maximum translation velocity may be increased while keeping the oscillation frequency constant by increasing the oscillation distance.

For example, the oscillation cylinder may linearly accelerate up to a translation velocity set point. The translational velocity set point may be determined by an operator and set according to viscosity properties of the fluid. For example, in certain embodiments, the translation velocity set point 308 may be from about 1 meter per hour to about 1000 meters per minute. The oscillation cylinder may be capable of simulating the shear forces applied to the fluid by pipe, tubing, and/or formation when pumped downhole.

In certain embodiments, a method for measuring the viscosity of a fluid, may comprise placing the fluid within a chamber defined by an inner surface of a cylinder and opposing stoppers of a first and second piston; oscillating the cylinder relative to a bob disposed within the chamber; sensing an axial shear force imparted to the bob; and determining the apparent viscosity of the fluid based on the axial shear force.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the patentee. The indefinite articles "a" or "an," as used in the claims, are defined herein to mean one or more than one of the element that it introduces.

What is claimed is:

1. A system for measuring the viscosity of a fluid, comprising:
    an oscillation cylinder having an inner surface;
    a first piston having a first stopper disposed within the oscillation cylinder and forming a seal with the inner surface;
    a second piston having a second stopper disposed within the oscillation cylinder and forming a seal with the inner surface;

a chamber defined between the first stopper and second stopper; and a bob formed within the chamber having a sensor which measures an axial shear force induced by the oscillation cylinder which is indicative of the apparent viscosity of the fluid in the chamber.

2. The system of claim 1, further comprising a motor capable of linearly translating the oscillation cylinder.

3. The system of claim 2, wherein the motor includes a stepper motor.

4. The system of claim 1, wherein the chamber comprises the fluid.

5. The system of claim 1, wherein the bob includes a load transducer.

6. The system of claim 1, further comprising a heater disposed adjacent to the oscillation cylinder and capable of heating the oscillation cylinder and the fluid.

7. The system of claim 1, further comprising a vortex generator.

8. The system of claim 7, wherein the vortex generator includes a fan attached to the second piston.

9. The system of claim 1, further comprising a rotation motor connected to the bob and capable of rotating the bob within the chamber.

10. A method for measuring the viscosity of a fluid, comprising:

placing the fluid within a chamber defined by an inner surface of a cylinder and opposing stoppers of a first and second piston;

oscillating the cylinder relative to a bob disposed within the chamber;

sensing an axial shear force imparted to the bob; and determining the apparent viscosity of the fluid based on the axial shear force.

11. The method of claim 10, wherein oscillating the cylinder includes moving the cylinder axially.

12. The method of claim 10, wherein oscillating the cylinder includes moving the cylinder between a first position and a second position at a set frequency.

13. The method of claim 10, further comprising mixing the fluid within the chamber.

14. The method of claim 10, further comprising increasing the pressure of the chamber to at least 2 atm.

15. The method of claim 10, further comprising heating the oscillating cylinder and the fluid.

16. A viscometer, comprising:

an oscillation cylinder having an inner surface, wherein the oscillation cylinder includes a fluid;

a fixed piston having a first stopper disposed within the oscillation cylinder and forming a seal with the inner surface;

an adjustable piston having a second stopper disposed within the oscillation cylinder and forming a seal with the inner surface;

a chamber defined between the first stopper and second stopper;

a bob formed within the chamber having a sensor which measures an axial shear force induced by the oscillating cylinder which is indicative of the apparent viscosity of the fluid in the chamber; and a motor capable of linearly translating the oscillation cylinder.

17. The viscometer of claim 16, wherein the bob includes a load transducer.

18. The viscometer of claim 16, further comprising a rotation motor connected to the bob and capable of rotating the bob within the chamber.

19. The viscometer of claim 16, further comprising a vortex generator connected to the adjustable piston.

20. The viscometer of claim 16, further comprising a heater disposed adjacent to the oscillation cylinder and capable of heating the oscillation cylinder and the fluid.

* * * * *